(12) United States Patent
You et al.

(10) Patent No.: US 10,172,777 B2
(45) Date of Patent: Jan. 8, 2019

(54) PHYTOSPINGOSINE DERIVATIVE AND COMPOSITION CONTAINING SAME

(71) Applicant: AMOREPACIFIC CORPORATION, Seoul (KR)

(72) Inventors: Jae Won You, Yongin-si (KR); Tae Hun Park, Yongin-si (KR); Yong-Jin Kim, Yongin-si (KR); Jon Hwan Lee, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 15/560,879

(22) PCT Filed: Mar. 14, 2016

(86) PCT No.: PCT/KR2016/002501
§ 371 (c)(1),
(2) Date: Sep. 22, 2017

(87) PCT Pub. No.: WO2016/159537
PCT Pub. Date: Oct. 6, 2016

(65) Prior Publication Data
US 2018/0116939 A1      May 3, 2018

(30) Foreign Application Priority Data
Mar. 31, 2015  (KR) .................. 10-2015-0044835

(51) Int. Cl.
| C07H 15/12 | (2006.01) |
| C07H 1/00  | (2006.01) |
| A61K 8/68  | (2006.01) |
| A61P 17/10 | (2006.01) |
| A61P 31/04 | (2006.01) |
| A61K 8/60  | (2006.01) |
| A61K 31/133| (2006.01) |
| A61Q 19/00 | (2006.01) |
| C07C 215/10| (2006.01) |
| C07H 15/04 | (2006.01) |

(52) U.S. Cl.
CPC ............... *A61K 8/68* (2013.01); *A61K 8/60* (2013.01); *A61K 31/133* (2013.01); *A61P 17/10* (2018.01); *A61P 31/04* (2018.01); *A61Q 19/00* (2013.01); *C07C 215/10* (2013.01); *C07H 15/04* (2013.01); *C07H 15/12* (2013.01)

(58) Field of Classification Search
None
See application file for complete search history.

(56) References Cited

U.S. PATENT DOCUMENTS

2007/0104774 A1    5/2007    Kim et al.

FOREIGN PATENT DOCUMENTS

| KR | 20020042606 A | 6/2002 |
| KR | 100343885 B1 | 7/2002 |
| KR | 20030014780 A | 2/2003 |
| KR | 100690103 B1 | 3/2007 |
| KR | 20130094547 A | 8/2013 |
| KR | 20140097263 A | 8/2014 |
| WO | 03097631 A1 | 11/2003 |
| WO | 03101937 A1 | 12/2003 |
| WO | WO-03101937 A1 * | 12/2003 | ........... C07C 215/24 |

OTHER PUBLICATIONS

International Search Report for International Application No. PCT/KR2016/002501. (dated Jul. 8, 2016) (9 Pages).
Pascher et al., "Synthesis of galactosylphytosphingosine and galactosylceramides containing phytosphingosine", Chemistry and Physics of Lipids, Limerick, IR, vol. 12, No. 4, Jul. 1, 1974, pp. 303-315.
Extended European Search Report, 16773318.7, dated Jan. 24, 2018.

* cited by examiner

*Primary Examiner* — Traviss C McIntosh, III
(74) *Attorney, Agent, or Firm* — Lucas & Mercanti, LLP

(57) ABSTRACT

The present invention relates to a phytospingosine derivative generated by a condensation reaction of phytospingosine and maltose or lactose, which is an aldose-based disaccharide, and to a composition containing the same. The phytospingosine derivative of the present invention has high solubility in water compared with phytospingosine, is easy to formulate since the stabilization problem in a solution is solved, and maintains or further enhances the antibacterial effect of phytospingosine.

6 Claims, 1 Drawing Sheet

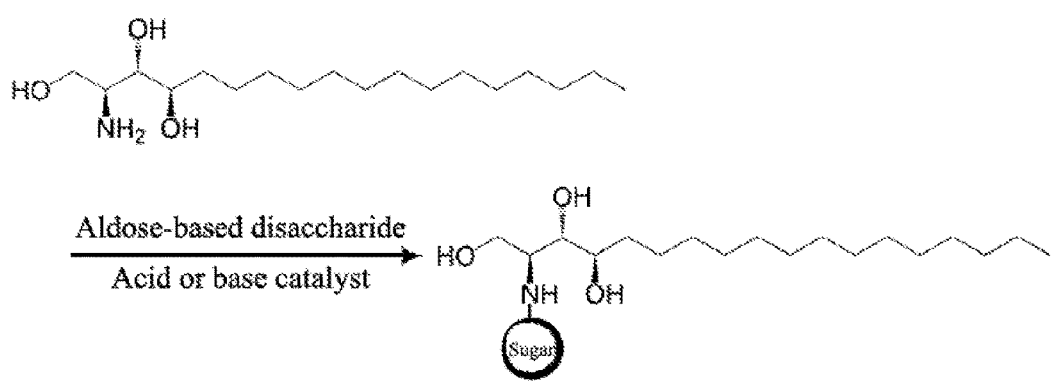

PHYTOSPINGOSINE DERIVATIVE AND COMPOSITION CONTAINING SAME

CROSS-REFERENCE TO RELATED APPLICATIONS

This application is a 371 of PCT/KR2016/002501, filed on Mar. 14, 2016 which claims the benefit of Korean Patent Application No. 10-2015-0044835, filed Mar. 31, 2015 the contents of each of which are incorporated herein by reference.

TECHNICAL FIELD

The present invention relates to a phytospingosine derivative and a composition including the same, and more particularly, to a phytospingosine derivative generated by a condensation reaction of phytospingosine and maltose or lactose, which is an aldose-based disaccharide, and to a composition including the phytospingosine derivative as an active ingredient.

BACKGROUND ART

As a component of cell membranes in the living body, a sphingolipid contains a basic backbone of sphingoid long-chain bases such as spingosine, phytospingosine, and sphinganine. It was found that phytospingosine is generated in the skin by decomposition of ceramaid by ceramidases, and is present at a content of approximately 1 to 2% in the stratum corneum. The phytospingosine is known to serve to have an antibacterial effect on exogenous microbes, alleviate skin inflammations and heal wounds in the skin. Also, it was found that the phytospingosine penetrates deep into the skin, and is used as a precursor for synthesis of ceramaid to promote the synthesis of ceramaid, and conformed that the phytospingosine inhibits protein-kinase C or phospholipase D to alleviate inflammations. Accordingly, the phytospingosine is effective in alleviating skin diseases accompanied by chronic inflammations such as atopy. In particular, it has been reported that the phytospingosine has a high antibacterial activity against *Staphylococcus aureus* (*S. aureus*) as a microbe often found in the atopic dermatitis, and *Propionibacterium acnes* (*P. acnes*) as a pathogen causing acne, compared to the antibiotics such as penicillin or erythromycin, is safe as a natural ingredient without any side effects, and is also effective in promoting the synthesis of collagen and the generation of epidermal cells.

The phytospingosine was first extracted from a plant, but has been often found recently in marine life, especially in mammalian tissues, as well as microbes such as fungi, yeast, etc. The phytospingosine currently used was generally extracted from the yeast *Pichai ciferrii*. However, such phytospingosine has limits in use for cosmetic and pharmaceutical applications due to problems regarding insolubility in water. As a plan to solve the problem regarding the water solubility of phytospingosine, Korean Registered Patent No. 0343885 discloses a method of preparing a transparent aqueous solution, which includes adding lactic acid and a willow bark extract to water without using a solvent such as an alcohol and dissolving phytospingosine, and Korean Registered Patent No. 0690103 discloses a method of preparing an aqueous solution using liposomes having a size of 100 nm or less and containing a high concentration of phytospingosine. However, the phytospingosine still has problems in use due to occurrence of precipitates when stored for a long period of time or a high viscosity of formulations.

The present inventors have conducted research in various aspects to solve the above problems, and found that, when phytospingosine and maltose or lactose, which is an aldose-based disaccharide, are used to synthesize a phytospingosine derivative, the phytospingosine derivative has an excellent antibacterial effect while making up for the drawbacks regarding the water solubility of phytospingosine, and a composition including the phytospingosine derivative has a superior function in improving and preventing bacterial skin diseases, inflammatory skin diseases, and autoimmune diseases as well. Therefore, the present invention has been completed based on these facts.

PRIOR-ART DOCUMENTS

Korean Registered Patent No. 0343885 "A Process For Preparing Phytosphingosine Aqueous Solution"

DISCLOSURE

Technical Problem

Because phytospingosine is insoluble in water, and also dissolved at a content of approximately 1% by weight even in a solvent such as isocetyl alcohol, which may be used as a source material for cosmetics, the phytospingosine has technical difficulties in being formulated at a sufficient amount to have an effect as a source material for functional cosmetics, and also has limits in use for cosmetic and pharmaceutical applications due to these problems regarding the water solubility of phytospingosine.

As a plan to enhance the solubility in water, there is a method of converting phytospingosine into the form of ammonium salts using an acid component. However, this method has a drawback in that an antibacterial effect of phytospingosine may be reduced. As another plan, there is a method including dissolving phytospingosine at a high temperature using a certain oil component and formulating the resulting solution of phytospingosine. However, this method also has a problem regarding the usability and has a drawback in that the phytospingosine may be precipitated in a formulation when stored at room temperature.

Accordingly, it is an aspect of the present invention to provide a phytospingosine derivative which is easy to formulate because the problems regarding the solubility in water are solved while maintaining an antibacterial effect of phytospingosine, and a composition including the same.

Technical Solution

Therefore, the present invention is designed to solve the above problems, and it is an aspect of the present invention to provide a phytospingosine derivative represented by the following Formula I or II, which is generated by a condensation reaction of phytospingosine and maltose or lactose, which is an aldose-based disaccharide, and a composition including the phytospingosine derivative as an active ingredient.

<Formula I>

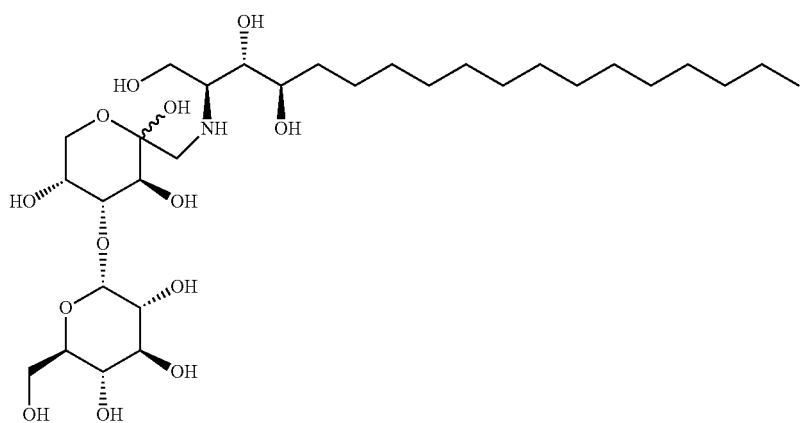

<Formula II>

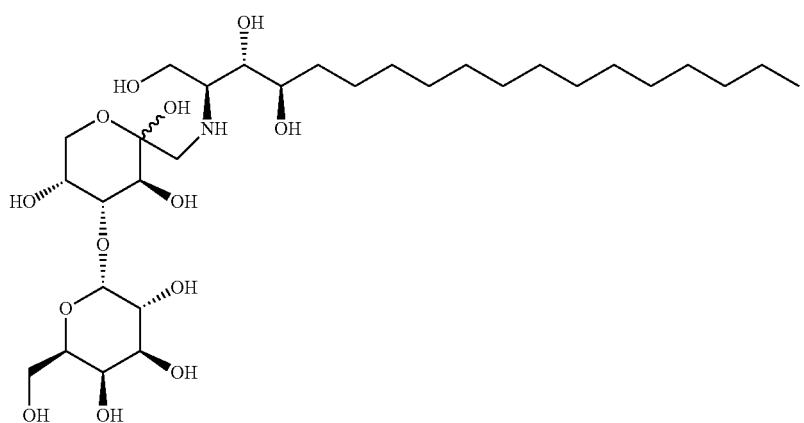

Advantageous Effects

The phytospingosine derivative of the present invention in which an aldose-based disaccharide is bound to phytospingosine has higher solubility in water than phytospingosine, and also has an effect of being easily formulated into skin preparations for external use without any additional technique for dissolving a conventional insoluble source material because the problems regarding the stabilization in a solution are solved.

The phytospingosine derivative of the present invention in which an aldose-based disaccharide is bound to phytospingosine has an excellent effect as an antibacterial preparation or a skin preparation for external use for improving skin diseases because the phytospingosine derivative maintains or further enhances the antibacterial effect of conventional phytospingosine.

The antibacterial composition or the skin preparation composition for external use for improving skin diseases has an effect of improving a diseased site of the skin, which develops various diseases such as atopic dermatitis, psoriasis, ringworm on hands and feet, trichophytia maculovesiculosa, various types of eczema, severe acne, pruritus, herpes zoster, psoriasis, chronic pruritus cutaneus, persistent palmoplantar pustulosis, dermatophytosis, malignant swelling, etc., into the normal skin.

DESCRIPTION OF DRAWINGS

FIG. 1 is a chemical scheme schematically showing a method of preparing a phytospingosine derivative according to the present invention.

BEST MODE

The present invention is directed to a phytospingosine derivative and a composition including the same, and more particularly, to a phytospingosine derivative generated by a condensation reaction of phytospingosine and maltose or lactose, which is an aldose-based disaccharide, and to a composition including the phytospingosine derivative as an active ingredient. Hereinafter, the present invention will be described in detail.

The term "derivative" used in the present invention generally refers to a compound obtained by chemically modifying a moiety of a certain compound, that is, a compound in which a hydrogen atom or a certain atomic group is replaced with another atom or atomic group. The "phytospingosine derivative" of the present invention refers to a substance having a structure represented by the following Formula I or II, which is formed by allowing maltose or lactose, which is an aldose-based disaccharide having a structure represented by the following Formula B or C, to chemically bind to phytospingosine having a structure represented by the following Formula A. In the present invention, the term "aldose-based disaccharide" refers to a disaccharide in which two aldose monosaccharides are bound to each other. For example, maltose in which two glucose molecules are bound to each other and lactose in which one glucose molecule is bound to one galactose molecule are applied as representative aldose-based hexoses.

The phytospingosine derivative having a structure represented by the following Formula I may be a product generated by a condensation reaction of phytospingosine and maltose, and the phytospingosine derivative having a structure represented by the following Formula II may be a product generated by a condensation reaction of phytospingosine and lactose. FIG. 1 is a chemical scheme schematically showing a method of preparing a phytospingosine derivative according to the present invention.

<Formula A>

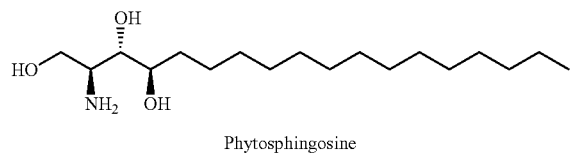

Phytosphingosine

<Formula B>

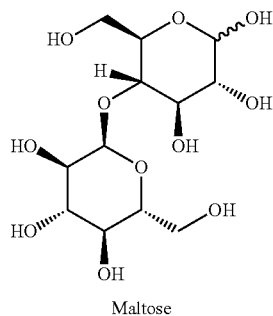

Maltose

<Formula C>

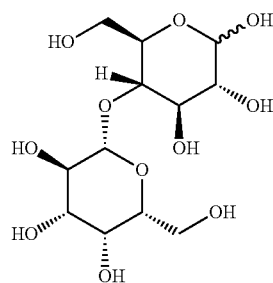

Lactose

<Formula I>

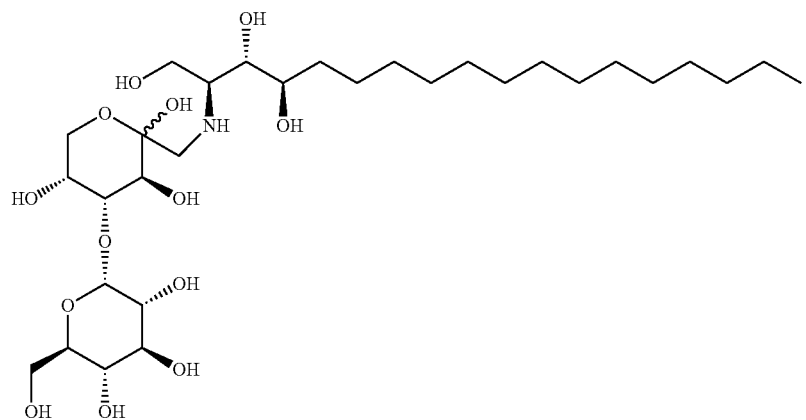

-continued

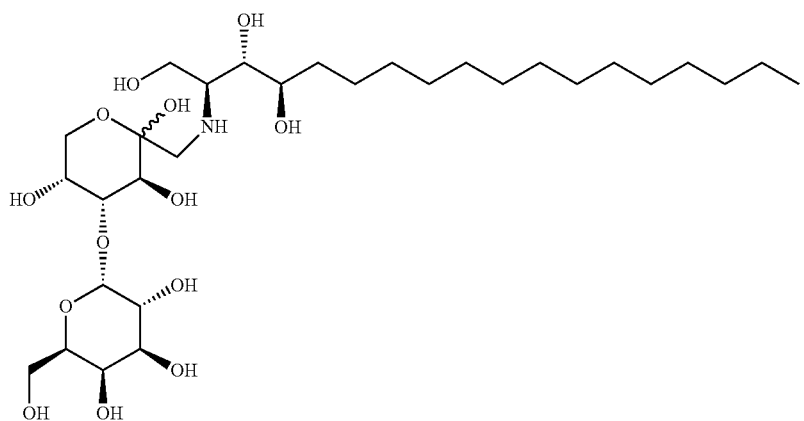
<Formula II>

To prepare the phytospingosine derivative having the structure of Formula I or II according to the present invention, a condensation reaction of the phytospingosine of Formula A and the aldose-based disaccharide of Formula B or C at a molar ratio of 1:0.8 to 1:1.2 is performed. In this case, the condensation reaction may be performed using an acid or base catalyst. More preferably, the phytospingosine reacts with the aldose-based disaccharide at a molar ratio of 1:1.05. In this case, the catalyst may be used at an equivalent content of 0.05 to 0.1. Also, a polar solvent may be used as a reaction solvent, and methanol or ethanol may be used as a lower alcohol, but the present invention is not limited thereto.

The composition of the present invention including the phytospingosine derivative having the structure of Formula I or II or a pharmaceutically acceptable salt as an active ingredient may be an antibacterial composition or a skin preparation composition for external use for improving skin diseases, and may be used as a skin preparation for external use in pharmaceuticals, cosmetics or washing, depending on formulations and purposes thereof. When the composition is used as a base material for skin preparations for external use, the blending ratio of the present invention is not particularly limited, and may, for example, be properly chosen depending on the shape, effect, and the like of the skin preparation for external use. The composition may be prepared into suitable formulations, for example, liquid-phase, gel-phase, paste-phase, cream-phase, powder-phase, and solid-phase formulations, using another skin base material for external use.

The skin preparation composition for external use of the present invention may be widely applied to cosmetic compositions applied to the epidermis or the dermis, hair compositions (for scalp and hair care), skin detergent compositions, pharmaceutical compositions, quasi-drug compositions, etc., and formulations thereof may be used without limitation as long as they can be applied to the skin. A solution, a soluble form such as a lotion, an emulsion such as a liquid cream or a cream, a powder dispersion, a water-oil two layer form, a water-oil-powder three layer form, a dispersion, an ointment, a gel, an aerosol, or any formulation used in conventional skin preparations for external use may be applied. The types and contents of the components used to prepare these formulations may be adjusted within a range known to persons having ordinary skill in the art.

Also, when the composition of the present invention is formulated into skin medicines for external use or skin cosmetics for external use, other components generally used herein such as a base material for external use, a surfactant, fat and oils, a moisturizing agent, a stabilizing agent, a preservative, a thickening agent, a pigment, a flavoring agent, a refreshing agent, or the like may be suitably mixed with the composition of the present invention.

The other base material for external use may, for example, include white petrolatum, cetanol, liquid paraffin, squalene, squalane, lanolin, a heavy-chain fatty acid triglyceride, etc., and the surfactant may, for example, include glycerin fatty acid ester, sucrose fatty acid ester, sorbitan fatty acid ester, lecithin, polyoxyethylene (POE)-hydrogenated castor oil, sodium laurate, etc. The stabilizing agent may, for example, include 4 or 2 alkali salts of ethylenediaminetetraacetic acid (EDTA), POE sorbitan fatty acid ester, etc. The preservative may, for example, include para-oxy benzoic acid ester, sorbic acid, phenol, benzyl alcohol, etc., the thickening agent may, for example, include Arabia gum, guar gum, carrageenan, carboxymethyl cellulose, a vinyl acetate resin emulsion, a polyacrylate, etc., and the flavoring and refreshing agents may, for example, include peppermint oil, eucalyptus oil, menthol, rose oil, lavender oil, orange oil, a vanilla flavor, a fruit flavor, vanillin, etc. A blending component which may be added herein is not limited to the aforementioned components, and any component may be blended in such a range that the objects and effects of the present invention are not hindered.

Also, the antibacterial composition or skin preparation composition for external use for improving skin diseases according to the present invention may include only the phytospingosine derivative having a structure of Formula I or II or a pharmaceutically acceptable salt as the active ingredient, or may further include one or more symptom-improving components or active therapeutic components for improving and treating skin diseases. For example, bufexamac, allantoin, glycyrrhizic acid dipotassium, lidocaine, and the like, all of which have an effect of alleviating pruritus, may also be blended.

MODE FOR INVENTION

Hereinafter, the present invention will be described in further detail with reference to specific embodiments thereof. However, it will be apparent to those skilled in the art that the present invention is not limited to the embodiments disclosed below, but various modifications and changes can be made to the aforementioned exemplary embodiments of the present invention without departing from the scope of the present invention. Also, unless otherwise defined in this specification, all the technical and scientific terms used herein have the same meanings as what are generally understood by a person skilled in the related art to which the present invention belongs. Therefore, repeated descriptions of the same technical configurations and operations as in the prior art are omitted for clarity.

Example 1: Synthesis of Phytospingosine Derivative 3.17 g of phytospingosine, 3.78 g of maltose monohydrate, and 30 μL of acetic acid were added to 40 mL of methanol (Me-OH), and reacted for 12 hours under reflux. After the reaction was completed, the resulting solution was cooled to room temperature, and acetone was added to the solution to precipitate a phytospingosine derivative. The precipitated phytospingosine derivative was filtered and dried.

$^1$H NMR (300 MHz, D$_2$O) δ: 0.89 (3H), 1.10-1.50 (26H), 2.90-3.20 (4H), 3.25-4.20 (14H), 4.66 & 5.20-5.45 (1H)

Example 2: Synthesis of Phytospingosine Derivative

A phytospingosine derivative was prepared in the same manner as in Example 1, except that lactose monohydrate was used instead of the maltose monohydrate.

$^1$H NMR (300 MHz, D$_2$O) δ: 0.89 (3H), 1.10-1.50 (26H), 2.90-3.20 (4H), 3.25-4.20 (14H), 4.66 & 5.20-5.45 (1H)

Experimental Example 1: Solubility Test for Phytospingosine Derivatives

Each of the phytospingosine derivatives obtained in Examples 1 and 2 was added at contents of 0.1% by weight and 1.0% by weight, based on the total weight of the aqueous solution, and dissolved in distilled water having a temperature of 50 to 60° C. Thereafter, the resulting solution was kept at room temperature to check a precipitation behavior over time. As Comparative Example, the same experiment was performed using phytospingosine. The results are listed in the following Table 1.

TABLE 1

|  | Example 1 | | Example 2 | | Comparative Example | |
| --- | --- | --- | --- | --- | --- | --- |
| Contents | 0.1% | 1.0% | 0.1% | 1.0% | 0.1% | 1.0% |
| 1 day | ○ | ○ | ○ | ○ | Δ | X |
| 7 days | ○ | ○ | ○ | ○ | X | X |
| 30 days | ○ | ○ | ○ | ○ | X | X |

○: Not precipitated
Δ: Not remarkably precipitated but fine particles are generated
X: Remarkably precipitated Looking at Table 1, it can be seen that the phytospingosine derivative of the present invention had improved solubility in water, compared to Comparative Example in which phytospingosine was used, and also had excellent stability in water because the phytospingosine derivative was not precipitated even when stored for a long period of time.

Experimental Example 2: Antibacterial Test for Phytospingosine Derivatives (1) Preparation of Test Bacterial Solution As six representative microbes (fungi, and bacteria) causing skin diseases, each of *Malassezia globosa, Malassezia restricta, Candia albicans* (*C. albicans*), *Aspergillus niger* (*A. niger*), *Enterococcus faecalis*, and *Brevundimonas vesicularis* was seeded in a *P. ovale* medium, and cultured at 32° C. for 3 days while stirring. The resulting culture broth was diluted with *P. ovale* at a density of 1.0×10$^7$ CFU/mL, and the diluted culture broth was used as a test bacterial solution.

(2) Preparation of Sample Solution

A suspension obtained by suspending the phytospingosine derivative prepared in Example 1 and 0.8% phytospingosine of Comparative Example in a *P. ovale* medium was used as a sample solution.

(3) Test Method

① 200 μL of the sample solution prepared in (2) was added to the first row of a 96-well plate. 100 μL of *P. ovale* was added to the other wells.

② After the first row of the mixtures were thoroughly mixed, 100 μL of each of the mixtures was taken, added to the second row, and then thoroughly mixed, and 100 μL of each of the mixtures was again taken, and added to the third row. Thereafter, this procedure was repeated to perform a double dilution.

③ After each of the microbes were cultured for 32 to 48 hours, a degree of suspension was used to determine whether the bacteria were growing. In this case, a minimal concentration at which the bacteria did not grow was defined as a minimum inhibitory concentration (MIC) value. When it was difficult to determine whether the bacteria were growing due to the opaque mixed solution, the growth of the bacteria was observed under a microscope.

The test results are listed in the following Table 2.

TABLE 2

|  | Example 1 | Comparative Example |
| --- | --- | --- |
| *Malassezia globosa* | 0.001954 | 0.001954 |
| *Malassezia restricta* | 0.001954 | 0.001954 |
| *C. albicans* | 0.0019 | 0.0312 |
| *A. niger* | 0.25 | 0.5 |
| *Enterococcus faecalis* | 0.0039 | 0.062 |
| *Brevundimonas vesicularis* | <0.00097 | <0.00097 |

From the results of the antibacterial test, it was revealed that the phytospingosine derivative of Example 1 had a superior antibacterial effect against *C. albicans, A. niger*, and *Enterococcus faecalis* among a total of the six microbes and had a similar antibacterial effect against the other three microbes, compared to the phytospingosine of Comparative Example.

From the results of the solubility test and antibacterial test, it can be seen that the phytospingosine derivative of the present invention in which maltose or lactose, which was an aldose-based disaccharide, was bound to phytospingosine had improved water solubility, and had a superior or similar antibacterial effect, compared to conventional phytospingosine.

The invention claimed is:

1. A phytospingosine derivative represented by the following Formula

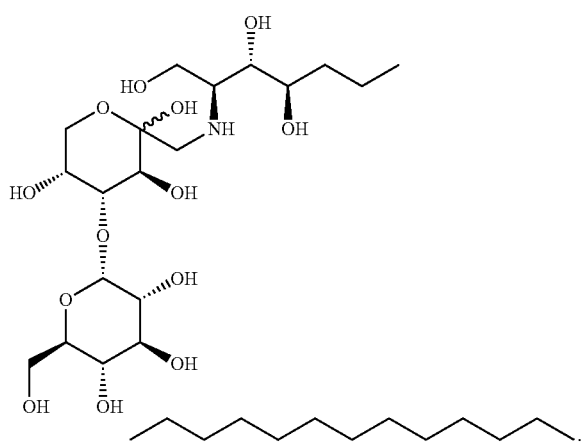

2. The phytospingosine derivative of claim 1, wherein the phytospingosine derivative is a product generated by a condensation reaction of phytospingosine and maltose.

3. An antibacterial composition or a skin preparation composition for external use for improving skin diseases comprising the phytospingosine derivative according to claim 1 or a pharmaceutically acceptable salt thereof as an active ingredient.

4. A method of preparing a phytospingosine containing compound to which an aldose-based disaccharide is bound, comprising:
   performing a condensation reaction of phytospingosine and an aldose-based disaccharide at a molar ratio of 1:0.8 to 1:1.2,
   wherein the aldose-based disaccharide is maltose or lactose.

5. The method of claim 4, wherein the condensation reaction is carried out in the presence of an acid catalyst.

6. The method of claim 4, wherein the condensation reaction is carries out in the presence of a base catalyst.

* * * * *